United States Patent
Hastings

(10) Patent No.: US 10,667,789 B2
(45) Date of Patent: Jun. 2, 2020

(54) LASER ASSISTED ULTRASOUND GUIDANCE

(71) Applicant: Geoffrey Steven Hastings, San Francisco, CA (US)

(72) Inventor: Geoffrey Steven Hastings, San Francisco, CA (US)

( * ) Notice: Subject to any disclaimer, the term of this patent is extended or adjusted under 35 U.S.C. 154(b) by 293 days.

(21) Appl. No.: 15/730,263

(22) Filed: Oct. 11, 2017

(65) Prior Publication Data

US 2019/0105017 A1 Apr. 11, 2019

(51) Int. Cl.
| | |
|---|---|
| *A61B 8/00* | (2006.01) |
| *A61B 5/00* | (2006.01) |
| *A61B 90/13* | (2016.01) |
| *A61B 10/02* | (2006.01) |
| *A61B 8/08* | (2006.01) |
| *A61B 5/06* | (2006.01) |

(Continued)

(52) U.S. Cl.
CPC .............. *A61B 8/46* (2013.01); *A61B 5/6851* (2013.01); *A61B 8/0841* (2013.01); *A61B 8/4444* (2013.01); *A61B 8/4455* (2013.01); *A61B 10/0233* (2013.01); *A61B 90/13* (2016.02); *A61B 5/0077* (2013.01); *A61B 5/061* (2013.01); *A61B 5/066* (2013.01); *A61B 10/0283* (2013.01); *A61B 2017/3413* (2013.01); *A61B 2090/378* (2016.02)

(58) Field of Classification Search
CPC ........... A61B 8/00; A61B 8/46; A61B 8/0833; A61B 8/0841; A61B 8/4263
See application file for complete search history.

(56) References Cited

U.S. PATENT DOCUMENTS

| | | |
|---|---|---|
| 6,689,067 B2 | 2/2004 | Sauer et al. |
| 6,702,749 B2 | 3/2004 | Paladini et al. |
| 8,162,852 B2 | 4/2012 | Norris |

(Continued)

OTHER PUBLICATIONS

Electronics Hub (Light Sensors, https://www.electronicshub.org/light-sensors/, Feb. 2, 2015).*

(Continued)

*Primary Examiner* — Carolyn A Pehlke
(74) *Attorney, Agent, or Firm* — Law Office of Alan W. Cannon

(57) ABSTRACT

An instrument monitoring apparatus includes a guide and sensing component configured to be attached to an ultrasound probe. The guide and sensing component includes a source of illumination configured to project a light beam into a light plane; and a light receiver aligned with the light plane and configured to quantify an amount of light reflected from an object in the light plane to the light receiver by receiving the amount of reflected light and converting it to an electrical signal. A control component includes a processor configured to receive the electrical signal from the light receiver, and based on a magnitude of the amount of light represented by the electrical signal, determine whether the object is sufficiently within the light plane. The processor instructs output of a first signal when it is determined that the object is sufficiently within the light plane. The processor instructs output of a second signal that is distinct from the first signal, when it is determined that the object is not sufficiently within the light plane.

21 Claims, 10 Drawing Sheets

(51) Int. Cl.
*A61B 17/34* (2006.01)
*A61B 90/00* (2016.01)

(56) References Cited

U.S. PATENT DOCUMENTS

| | | |
|---|---|---|
| 2008/0027325 A1 | 1/2008 | Brooks et al. |
| 2009/0054790 A1* | 2/2009 | Czaniera ............. A61B 1/2673 600/476 |
| 2009/0247876 A1 | 10/2009 | Cannon, Jr. et al. |
| 2010/0106015 A1 | 4/2010 | Norris |
| 2011/0245659 A1 | 10/2011 | Ma et al. |
| 2013/0218024 A1* | 8/2013 | Boctor .................. A61B 34/20 600/476 |
| 2016/0296179 A1 | 10/2016 | Thompson et al. |

OTHER PUBLICATIONS

David Williams (Design a Luxmeter Using a Light Depenent Resistor, https://www.allaboutcircuits.com/projects/design-a-luxmeter-using-a-light-dependent-resistor/, Dec. 13, 2015).*
Live Science (How Do Digital Cameras Work, https://www.livescience.com/33789-digital-cameras-work-llmmp.html, 2012).*
Geffen et al., "A needle guidance device compared to free hand technique in an ultrasound-guided interventional task using a phatom", Anaesthesia, 2008, 63, pp. 986-990.
Liua et al., "Laser assisted ultrasound guided aspiration improves procedure time and reduces number of withdrawals>" Ultrasonics Vo. 48, Issue 8, Dec. 2008, Abstract.

* cited by examiner

LASER ASSISTED ULTRASOUND GUIDANCE

BACKGROUND OF THE INVENTION

Ultrasound is useful not only as a modality to detect and diagnose abnormalities, but also as a way to guide interventions such as biopsies, vascular access, tumor ablations, and drainage of fluid collections, body cavities, bile ducts, the urinary tract, and so on. FIG. 1 is an illustration of an ultrasound-guided biopsy as currently practiced. An ultrasound probe 1000 is placed against the skin of a patient in a location overlying a target 1002 within the body of the patient, so that ultrasound energy can be directed to the target for use in ultrasonic imaging of the target 1002 according to known principles.

A needle 1004 is advanced through the skin 1006 of the patient and is advanced toward the target 1002 and into the target 1002 with visual guidance provided by viewing the ultrasound imaging provided by the ultrasound probe 1000. The needle 1004 can be visualized in the ultrasound image from the time that it enters the ultrasound beam 1008 so that the image is useful in guiding the needle to the location of the target 1002, as the operator can manually make adjustments to the path along which the needle 1004 takes in reaching the target 1002.

Guiding the needle 1004 into the desired structure (i.e., target 1002) is a skill that requires the operator to decide on the best path to the target 1002 and insert the needle 1004 along that path. This process is greatly facilitated by lining up the needle 1004 in the plane of the ultrasound beam 1002. When the needle is in this plane, it appears as a straight, echogenic (bright) structure with a predictable trajectory toward the target, such as shown in FIG. 2. When the needle 1004 is not in this plane, it may appear as a bright dot where it crosses the ultrasound beam 1008 or not at all if it is completely outside the ultrasound beam 1008. In the case where the needle 1004 and its path are not seen in the ultrasound image, or is seen as crossing the ultrasound image, there is a risk that the needle 1004 may have passed through some unforgiving non-target anatomical structure.

The task of positioning the needle 1004 in the correct plane (plane of the ultrasound beam 1008) can be difficult because the ultrasound probe is a curvy hand-held device and the beam 1008 is not visible to the naked eye. The operator must estimate where the beam 1008 will be, insert the needle 1004, and readjust as necessary based on the appearance of the image. Gaining proficiency with this takes time and experience as it involves approximation, abstract thinking, and hand-to-image coordination. Lining up the needle 1004 can be done with the aid of a metallic or molded plastic guide, but most experienced operators do not use guides because they are expensive, clunky, easy to lose, and restrict the ability to reposition the needle 1004 pathway that the needle travels along. Also, since they clamp on the outside of the ultrasound probe, they must be discarded or re-sterilized between uses. Instead, most experienced operators work "free hand", relying on their many hours of experience and even so often endure repeated readjustments of the needle 1004 and ultrasound probe 1000 to reach the target 1002.

Because of these issues, various attempts have been made in the past to help facilitate the process of aligning the needle with the ultrasound beam and, ultimately, the target.

Ma et al., U.S. Patent Application Publication No. 2011/0245659 discloses a laser emitter 22 on an instrument portion 19 such as a syringe that is used to hold needle 14. Laser light emitted from the laser emitter 22 can be received or reflected by the receiver/reflector 23 on the ultrasound device 21. The transducers 22 and 23 are adapted to operate cooperatively to provide information regarding the depth of the tip of the instrument. Ma et al. also uses a needle guide 13 which restricts the location at which the needle can be inserted into the patient to a very small locus. Although one of the position transducers may comprise a reflector or other passive element, the invention of Ma et al. nevertheless requires specialized instrumentation, in addition to the ultrasound transducer and its position transducer, in order to be operable. Also, the calculations performed by the Ma et al. invention are focused on the depth of the tip of the instrument and do not provide information as to the accuracy of alignment of the needle 14 with the plane of the ultrasound imaging, as the guide 13 is used to provide information with respect to the orientation of the instrument with respect to the imaging transducer 21.

Brooks et al., US. Patent Application Publication No. 2008/0027325 discloses an ultrasound apparatus with a light source that emits a broad planar light beam that is coplanar with the target plane of the ultrasound beam. The needle is inserted into the plane of the laser beam so as to be collinear with the target beam. The operator can monitor light reflected from the needle to align the needle appropriately. However this requires the operator to take his eyes away from viewing the ultrasound image as the operator views the needle to see if light is reflecting off it. The operator must switch between viewing the needle directly and viewing the ultrasound image to coordinate both maintaining the needle in alignment with the light plane and observing the tip of the needle as it approaches the target. This requires additional skill and experience, as the operator must steady the needle position and have a good memory of the hand-to-eye coordination that was required to maintain that position of the needle upon viewing it, as the operator switches from viewing the needle directly to viewing the target on the ultrasound image. It can be difficult to maintain the orientation of the needle upon switching back and forth between views.

Sauer et al., U.S. Pat. No. 6,689,067 discloses an ultrasound probe 12 having a mounting unit 16 to which a laser light source 22 is affixed. The light source 22 can project a beam that is coplanar with the ultrasound imaging plane 4. A needle can be inserted into the skin of a patient along the laser line projected on the skin. The user can see if the needle is aligned with the laser beam plane/ultrasound imaging plane 4 by seeing a reflection of the light beam 3 off the surface of the needle. However this requires the operator to take his eyes away from viewing the ultrasound image as the operator views the needle to see if light is reflecting off it. The operator must switch between viewing the needle directly and viewing the ultrasound image to coordinate both maintaining the needle in alignment with the light plane and observing the tip of the needle as it approaches the target. This requires additional skill and experience, as the operator must steady the needle position and have a good memory of the hand-to-eye coordination that was required to maintain that position of the needle upon viewing it, as the operator switches from viewing the needle directly to viewing the target on the ultrasound image. It can be difficult to maintain the orientation of the needle upon switching back and forth between views. In another embodiment, an augmented reality system is used to see both the optical light beam or an optical image with overlaid markers and the patient at the same time. This involves a half silvered mirror and mounting elements which add to the expense and complexity of the apparatus.

There is a continuing need for improvements for facilitating the insertion and guidance of a needle into a desired target within a body with the assistance of imaging.

It would be beneficial to provide such improvements so that they can be used with needles that do not require additional specialized features or instrumentation to be used with the guidance system.

It would be further desirable to provide improvements that can be used to adapt existing imaging instrumentation for use in carrying out improved placement and/or guidance.

SUMMARY OF THE INVENTION

According to an aspect of the present invention, an assembly for guiding a needle or other instrument includes: an imaging component comprising a transducer that projects a planar imaging beam into an imaging plane; an instrument monitor comprising a source of illumination that projects a light beam into a light plane and a light receiver aligned with the light plane and configured to quantify an amount of light reflected from an object in said light beam to the light receiver; a processor configured to determine whether the object is aligned in the light plane, based upon a quantity of light received by the light receiver; and output means configured to output information to notify a user whether the object is aligned in the light plane, without the user needing to look at the object.

In at least one embodiment, the transducer comprises an ultrasound transducer that projects a planar ultrasound beam into an ultrasonic imaging plane.

In at least one embodiment, the light receiver comprises a photoresistor.

In at least one embodiment, the output means comprises a visual indicator, wherein a first visual indication is displayed when the object is aligned in the light plane and a second visual indication, different from the first visual indication, is displayed when the object is not aligned in the light plane.

In at least one embodiment, the output means comprises an audio indicator, wherein a first audio signal is outputted when the object is aligned in the light plane and a second audio signal, different from the first audio signal, is outputted when the object is not aligned in the light plane.

In at least one embodiment, the instrument monitor further includes: a camera oriented to view the object and a guide line projected onto the skin of a patient by the light beam; and a display configured to display images taken by the camera.

In at least one embodiment, a display is configured to display images generated by the imaging component, wherein the display configured to display images taken by the camera is positioned adjacent to, or integrated with the display configured to display images generated by the imaging component.

In at least one embodiment, the instrument monitor is oriented relative to the imaging component such that the imaging plane is coplanar with the light plane.

In at least one embodiment, the instrument monitor is oriented relative to the imaging component such that the imaging plane is out of plane relative to the light plane.

In at least one embodiment, the instrument monitor is oriented relative to the imaging component such that the imaging plane is normal to the light plane.

According to another aspect of the present invention, an instrument monitoring apparatus includes: a guide and sensing component configured to be attached to an ultrasound probe; the guide and sensing component including: a source of illumination configured to project a light beam into a light plane; and a light receiver aligned with the light plane and configured to quantify an amount of light reflected from an object in the light plane to the light receiver by receiving the amount of light and converting the amount of light to an electrical signal; and a control component. The control component includes: a processor configured to receive the electrical signal from the light receiver, and based on a magnitude of the amount of light represented by the electrical signal, determine whether the object is sufficiently within the light plane; and output means, wherein the processor instructs the output means to output a first signal when it is determined that the object is sufficiently within the light plane, and wherein the processor instructs the output means to output a second signal that is distinct from the first signal, when it is determined that the object is not sufficiently within the light plane.

In at least one embodiment, the light receiver comprises a photoresistor.

In at least one embodiment, the guide and sensing component further includes a camera oriented to view the object and a guide line projected onto the skin of a patient by the light beam; and the control component further includes a display configured to display images taken by the camera.

In at least one embodiment, the output means includes a speaker.

In at least one embodiment, the output means includes lights.

In at least one embodiment, the lights includes a first light configured to illuminate in a first color, and a second light configured to illuminate in a second color different from the first color.

According to another aspect of the present invention, a method of guiding an instrument to a target location inside a body of a patient includes: contacting an ultrasound probe to skin of the patient and positioning the ultrasound probe so that the target is shown in a display of an ultrasound system that includes the ultrasound probe; displaying a visible guide line on the surface of the patient's skin by emitting a light beam from an instrument monitoring apparatus mounted on or integral with the ultrasound probe; contacting the instrument to the skin of the patient at a location along the guide line; orienting the instrument so that the instrument is sufficiently in a plane of the light beam, as confirmed by at least one of an audible or visual feedback signal outputted by the instrument monitoring apparatus in a manner such that an operator of the ultrasound system does not have to interrupt viewing of the display of the ultrasound system in order to interpret the at least one audible or visual feedback signal; inserting the instrument through the skin and toward the target; wherein light rays emitted by the instrument monitoring apparatus that impact the instrument and are reflected back to a light receiver of the instrument monitoring apparatus are converted to electrical signals representative of amounts of light reflected from the instrument, and the electrical signals are continually monitored by a processor of the instrument monitoring apparatus during the inserting; wherein the processor instructs a first audible and/or visual feedback signal to be outputted when it is determined that the amount of light reflected is representative of the instrument being sufficiently in the light plane; wherein the processor instructs a second audible and/or visual feedback signal that is distinguishable by the user from the first audible and/or visual feedback signal, to be outputted when it is determined that the amount of light reflected is representative of the instrument being insufficiently in the light plane. The inserting and orientation adjustment may be temporarily halted any time that the second signal is outputted, with the adjusting continuing until such time as the first signal is again outputted. The inserting and adjusting as needed can then be continued, until the target is contacted or pierced by the instrument, as verified by ultrasonic imaging viewed on the display of the ultrasound system.

In at least one embodiment, a plane of an ultrasound beam emitted by the ultrasound probe is coplanar with a plane of the light beam.

In at least one embodiment, a plane of an ultrasound beam emitted by the ultrasound probe is normal to a plane of the light beam.

In at least one embodiment, a plane of an ultrasound beam emitted by the ultrasound probe is not coplanar with or normal to a plane of the light beam.

In at least one embodiment, the instrument monitoring apparatus further includes a camera and a camera display configured to display images taken by the camera, the method further comprising viewing the instrument and the guide line by the camera pm the camera display, wherein the camera display is positioned in a location for viewing by the operator without having to discontinue viewing the display of the ultrasound system.

In at least one embodiment, the method further includes calibrating the instrument monitoring apparatus, prior to the inserting, wherein the calibrating includes: aligning the instrument in the plane of the light beam, after the contacting the instrument to the skin, by directly visually confirming an orientation where the instrument appears brightest, due to a maximum amount of light reflected from the instrument; and angling the instrument in and out of the light beam by varying degrees; wherein an amount of light received by the light receiver when the instrument is in the plane is converted to a signal representative of a maximum amount of light that will be received by the light receiver, and light amounts reflected by the various positions wherein the instrument is angled to various degrees out of the line plane are converted to signals representative of the varying lesser amounts of light that are received by the light receiver resulting from the varying positions; wherein the signals converted by the light receiver are sent to the processor, and the processor establishes a range of signals corresponding to a range of light intensity values that will be received by the light receiver during normal use; and wherein the processor subdivides the range of signals to a subset of the range that indicates that the instrument is sufficiently within the light plane, and at least one subset of the range that indicates that the instrument is not sufficiently within the light plane.

In at least one embodiment, the instrument includes a needle.

These and other advantages and features of the invention will become apparent to those persons skilled in the art upon reading the details of the systems, apparatus and methods as more fully described below.

BRIEF DESCRIPTION OF THE DRAWINGS

In the course of the detailed description to follow, reference will be made to the attached drawings. These drawings show different aspects of the present invention and, where appropriate, reference numerals illustrating like structures, components, materials and/or elements in different figures are labeled similarly. It is understood that various combinations of the structures, components, materials and/or elements, other than those specifically shown, are contemplated and are within the scope of the present invention.

DETAILED DESCRIPTION OF THE INVENTION

Figure 1:
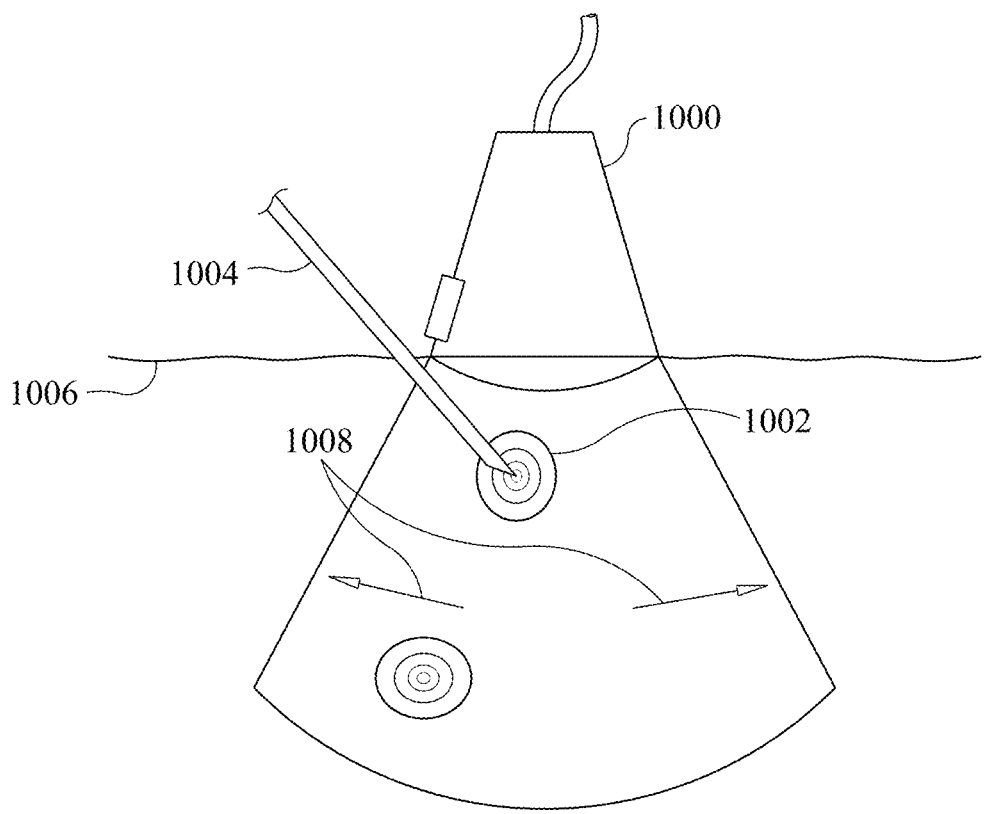
FIG. 1 is a schematic illustration showing use of an ultrasound probe to guide a needle to a target within a patient.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a processor" includes a plurality of such processors and reference to "the output means" includes reference to one or more output means and equivalents thereof known to those skilled in the art, and so forth.

The publications discussed herein are provided solely for their disclosure prior to the filing date of the present application. The dates of publication provided may be different from the actual publication dates which may need to be independently confirmed.

The present invention uses a light plane to show an operator the correct plane of entry of a needle or other instrument into a patient so that it is oriented in the plane of an ultrasound beam for visualization via ultrasound guidance. Output means are also provided to provide feedback to the operator as to whether the needle or other instrument is properly positioned for visualization via ultrasound imaging. In a preferred embodiment, the light plane is produced by a laser source that fans out the laser output to provide a visible line on the patient into which the needle or other instrument is to be inserted.

Figure 3:
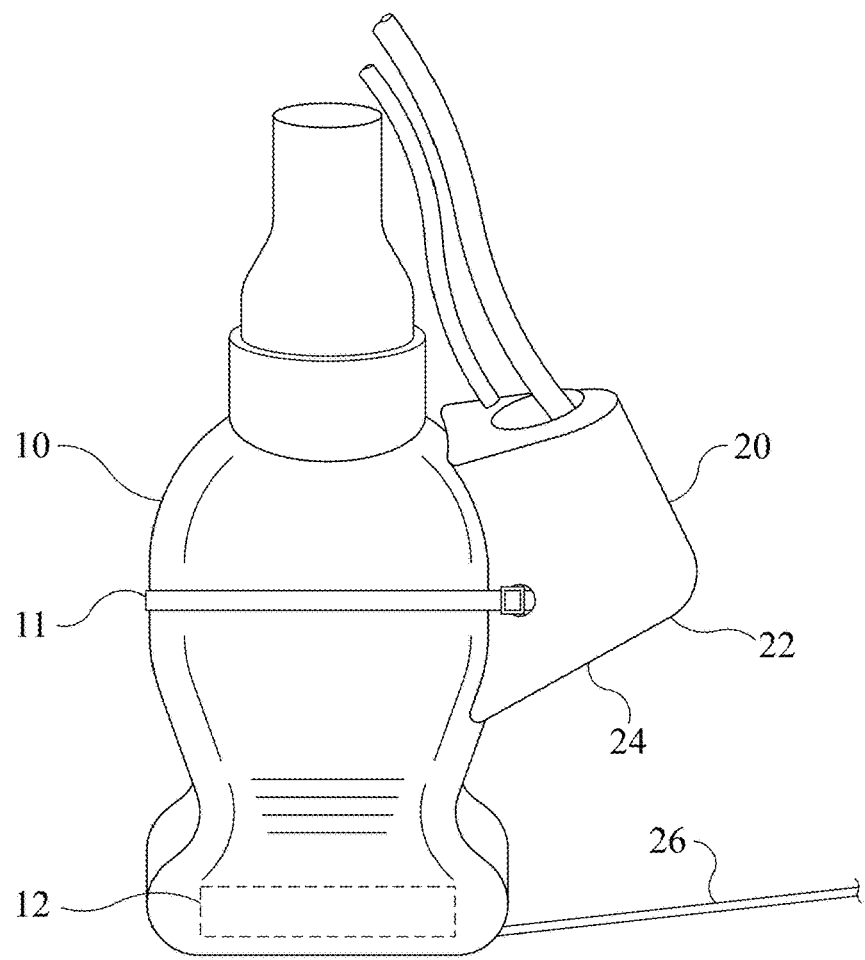
FIG. 3 shows an apparatus for guiding insertion of a needle or other instrument, according to an embodiment of the present invention.

Referring to FIG. 3, a guide and sensing component 20 of an apparatus 100 for guiding insertion of a needle or other instrument, according to an embodiment of the present invention is shown mounted to an ultrasound probe 10. In regard to this and all other embodiments of the invention, a needle refers to any type of needle used for medical procedures, including, but not limited to needles used for core or aspiration biopsy, venous access, targeted injection of therapeutic agents such as anesthetics for nerve blocks and a wide array of needle-shaped reflective metallic instruments such as radio frequency ablation probes, microwave ablation probes, cryoablation probes, drills, and instruments for delivering marking devices such as needle localization devices or fiducial markers. Other instruments include, but are not limited to any reflective, straight/cylindrical-shafted device that is not one of needles mentioned previously.

The ultrasound probe 10 can be an imaging probe 10 which includes an ultrasound transducer 12 configured to project a planar ultrasound beam into an ultrasonic imaging plane. In one non-limiting example, as ultrasound probe 10 used was a ZONARE L10-5 Linear Array Ultrasound Transducer, from Zonare Medical Systems, Inc., Mountain View, Calif. Of course the present invention is not limited to this specific embodiment as many other brands and types of ultrasound probes may be substituted.

Figure 4:
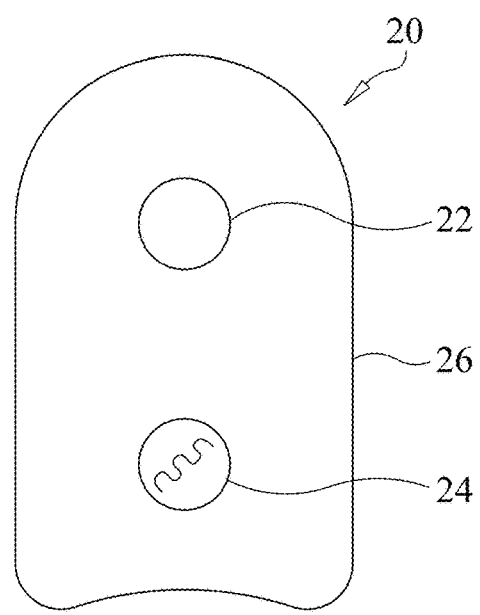
FIG. 4 is an end view of the guide and sensing component shown in FIG. 3.

Guide and sensing component 20 includes a source of illumination 22 (better shown in FIG. 4) that projects a light beam into a light plane and a light receiver 24 aligned with the projected light plane and configured to quantify an amount of light reflected from an object in the light plane to the light receiver 24. In the embodiment of FIGS. 3-4, and all other embodiments described herein, the source of illumination 22 is preferably a laser light emitter, but other sources of illumination, such as fluorescent, incandescent, light emitting diodes or the like could possibly be substituted. In one specific embodiment, a source of illumination 22 used was a Laserglow brightline economy ref line projecting alignment laser, available from Laserglow Technologies, Toronto, Ontario, Canada. In the embodiment of FIGS. 3-4, and all other embodiments described herein, the light receiver 24 is preferably a photoresistor, although other types of light receivers configured to quantify an amount of reflected light received could be substituted. One specific, non-limiting example used a SUNKEE Photo Light Sensitive Resistor Photoresistor Optoresistor 5 mm GM5539 5539, available from amazon.com. Of course, many other substitute light receivers could be used alternatively.

Figure 5:
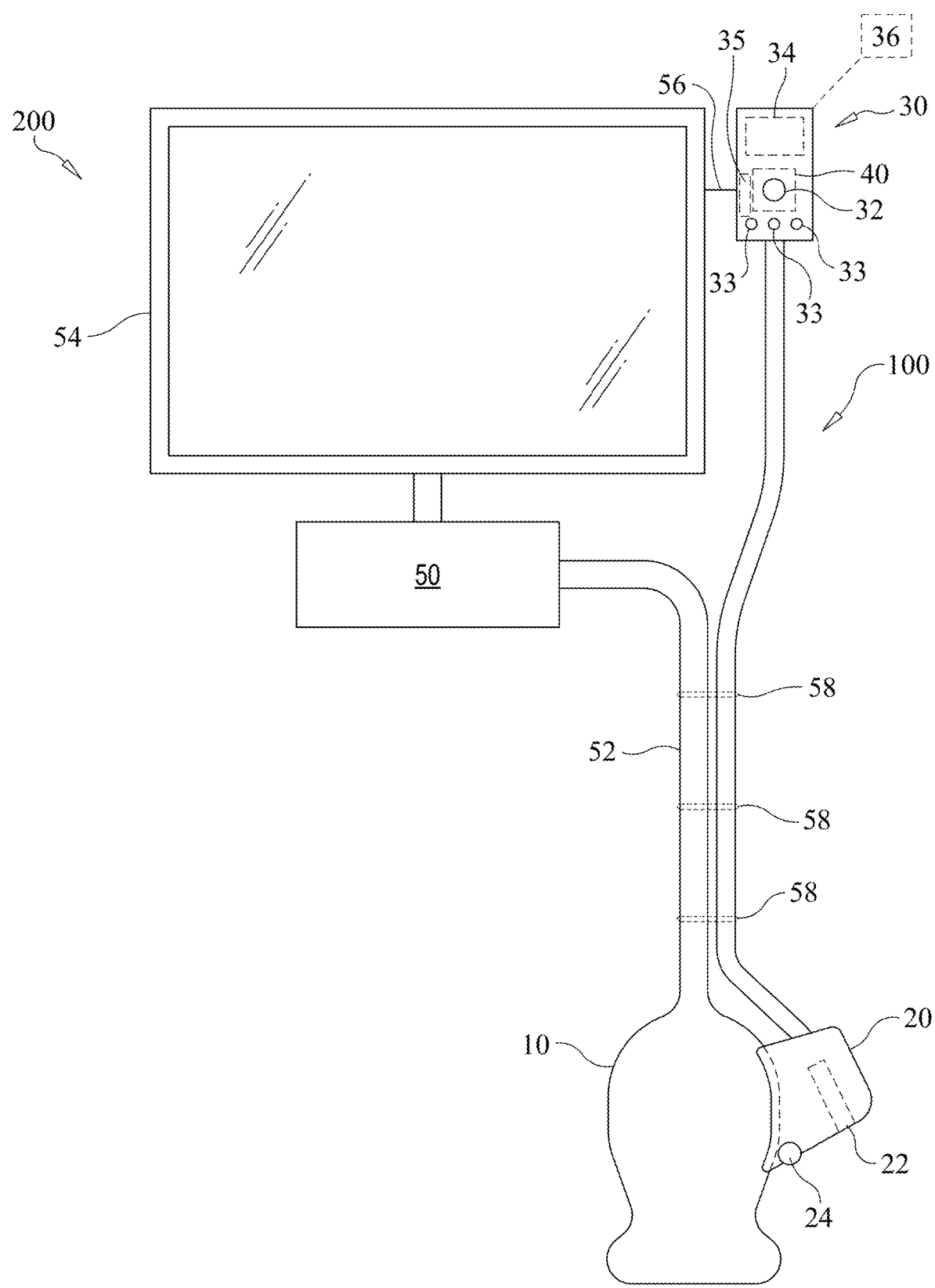
FIG. 5 is a schematic illustration of a system employing apparatus for guiding insertion of a needle or other instrument, according to an embodiment of the present invention.

FIG. 5 is a schematic illustration of a system 200 employing apparatus 100 for guiding insertion of a needle or other instrument, according to an embodiment of the present invention. Guide and sensing component 20 can be either removably or irremovably attached to probe 10, such as by mechanical means and/or chemical means (e.g., strapping, bolting, screwing and/or adhesives, etc.) or may be made integral with the probe 10. Guide and sensing component 20 is electrically communicates with control component 30. In the embodiment of FIG. 5, control component 30 includes processor 40, speaker 32, visual indicators 33 and optionally, a display 34, each of which are electrically connected to processor 40 for control thereby. A power source 35 is provided for powering both the control component 30 and the guide and sensing component 20. Alternatively, the guide and sensing component may have its own power source separate from the power source 35 supplying the control component 30. The control component 30 may be battery powered, in which case control component may further include a battery 35 electrically connected for powering the processor 40 and all other elements of the control component, as well as the guide and sensing component. Alternatively, the power source may include an external power source 36 such as an AC or DC power supply.

In the embodiment shown in FIG. 5, a battery power supply 35 is contained within the control component. A cable 38 interconnects the control component 30 and the guide and sensing component and functions to supply power and control instructions from the control component 30 to the guide and sensing component, such as for operating the light emitter 22. The cable also functions to send feedback from the light receiver 24 to the controller 40.

The ultrasound probe 10 is connected to the processor 50 of the ultrasound system via cable 52 and an ultrasound display 54 is operable to display ultrasound images resulting from signals received from the probe 10 and processed by the processor 50 according to currently known methods. The control component 30 may optionally be attached to the display 54 or any other part of the ultrasound system by an attachment mechanism such as any mechanical and/or adhesive type of attachment, or remain free of the display 54. Further optionally, cables 38 and 52 can be tied together or otherwise attached at one or more locations along their lengths. FIG. 5 illustrates optional ties 58 used for the purpose described.

Figure 6:
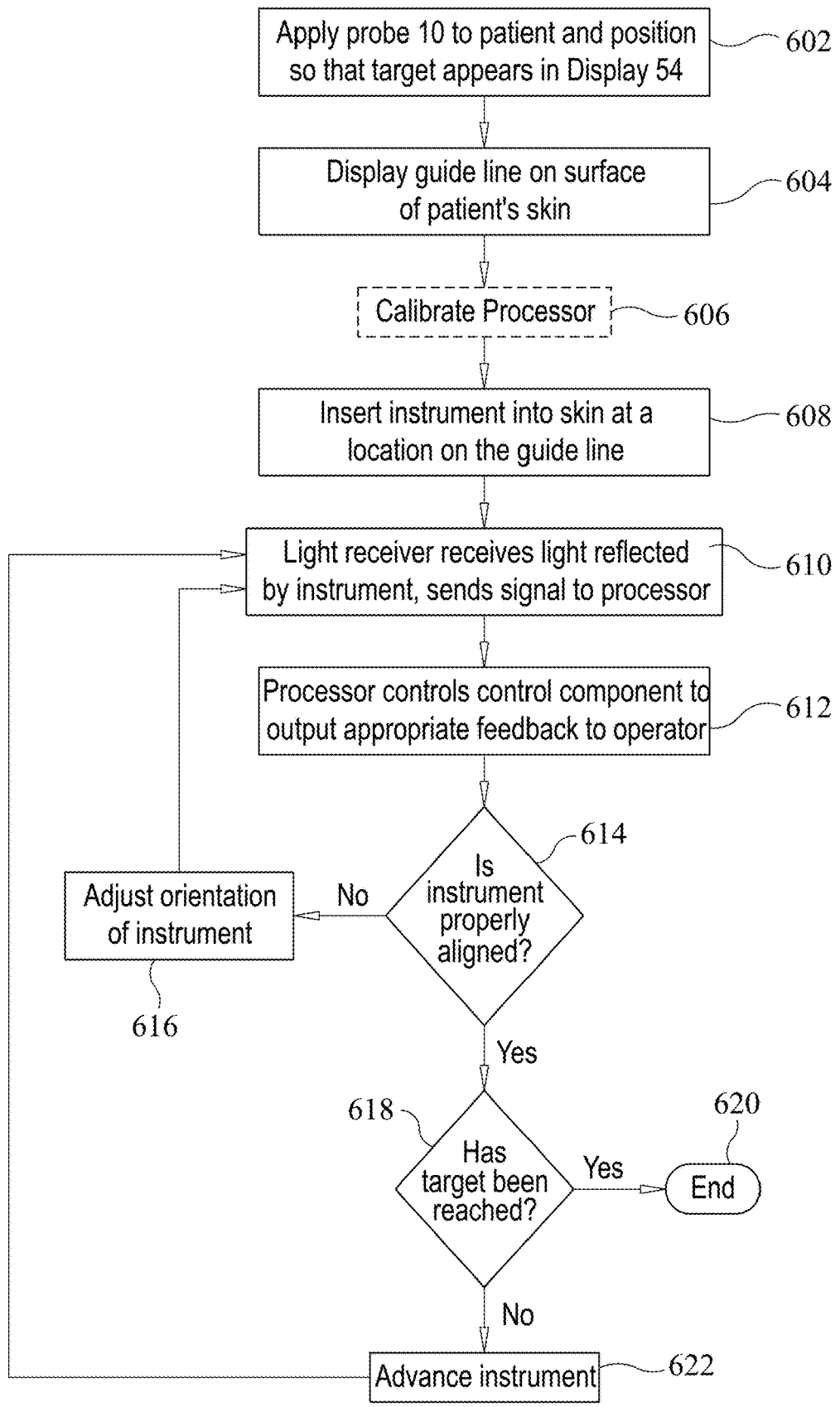
FIG. 6 shows events that can be carried out during a method of guiding an insertion of a needle or other instrument, according to an embodiment of the present invention.

FIG. 6 shows events that can be carried out during use of the system 200, according to an embodiment of the present invention. At event 602, the ultrasound system is prepared according to currently accepted practices and the probe 10 is applied to the skin of a patient and positioned appropriately so that a target to be pierced by a needle is shown in the display 54. Apparatus 100 is powered up and a guide line 26 (in the form of a laser line in this case) is emitted from light emitter 22 and displayed on the surface of the patient's skin at event 604 (see also FIG. 3). The light or laser emitter 22 makes this line by producing and emitting a fan-shaped beam. This fan-shaped beam defines a plane. The ultrasound probe 10 produces an ultrasound beam that defines a plane. The guide and sensing component 20 in the embodiments of FIGS. 3 and 5 is positioned relative to the probe 10 such that the plane of the fan-shaped beam of light or laser emitter 22 is coplanar with the plane of the fan-shaped ultrasound beam. This arrangement therefore results in the guide line 26 being coplanar with the plane of the fan-shaped ultrasound beam. As a result, the guide line 26 provides a continuum of locations along the skin of the patient (those locations underlying the guide line 26) into which a needle can be inserted so that will be in the plane of the ultrasound beam and therefor can be readily seen on the ultrasound image shown on the display 54 as it is advanced toward the target.

Optionally, at event 606, if the apparatus 100 has not already been calibrated, a needle 1004 or other instrument to be used in the procedure is used to calibrate the apparatus 100. In order to map out a range of high to low amounts of reflected light received by the light receiver (which converts the light received to electrical signals representative of the quantity of light received and feeds these signals back to the processor 40) and subdivide it into high, medium and low ranges for use in actuating various visual and/or audible indicators that indicate the relative amount of light being received by the light receiver 24 and thus indicating the relative degree to which the instrument 1004 is aligned within the light plane/ultrasound plane. Of course, the present invention is not limited to subdivision into three ranges, as two, or more than three ranges could be subdivided during the calibration. Subdivisions may be made to provide equal ranges or unequal. For example, the range indicating that the needle or other instrument 1004 is adequately aligned with the light plane may be smaller than one or more other ranges. As one non-limiting example, green, yellow or red indicator lights can be lit when, for example, the instrument 1004 is well aligned (green) less well aligned or only partially aligned (yellow) or even less-well aligned or nearly completely out of alignment (red). Additionally or alternatively, high, medium or low tones can be emitted by speaker 32 when instrument 1004 is well aligned (e.g., high tone), partially aligned (e.g., medium tone) or poorly aligned or nearly completely out of alignment (e.g., low tone). Further alternatively or additionally, a flashing visual indicator can be used to indicate various degrees of acceptable alignment. For example, a flashing indicator can be used when the instrument is not in an acceptable range of alignment and the flashing indicator can convert to a steady light when the instrument is within the acceptable bounds for alignment. Further alternatively or additionally, tones being played could be intermittent or pulsed, with the rate of the sound pulses increasing as the instrument becomes increasingly more out of alignment, and with the sound pulses converting to a steady tone when the instrument is within the acceptable bounds for alignment.

During calibration, a predetermined time period (in one non-limiting example, 5 seconds, but this could be less or more than 5 seconds) is provided prior to starting normal use of the apparatus. The needle 1004 or other reflective instrument to be used is placed at the skin 2 in the light plane of the light emitter, at the location along 26 and at approximately the angle α that the operator expects to use when inserting the instrument 1004 into the patient 1 during the procedure. The operator can readily visibly discern, by direct observation of the needle/instrument 1004 when it is most aligned in the light plane as this is when it appears brightest. This orientation establishes the maximum reflected light to be received by the light receiver 24, and calibration is commenced. During calibration, the operator moves the needle/instrument 1004 by angling it in and out of the light beam, gradually, by varying degrees. The light reflected off the needle/instrument 1004 at these various orientations and received by the light receiver, converted and fed back to the processor 40, establishes the range of light intensity values that will be received by the light receiver during normal use, and the device then switches to normal use mode. Angling the needle/instrument 1004 back and forth in a plane that is perpendicular to the light plane causes a large change in the amount of reflected light. This is the motion that is used for calibration, and it is this kind of alignment challenge that the present invention addresses. Angling the needle/instrument 1004 up and down within the light plane causes a much smaller change in the amount of reflected light. Once the operator locks on the correct back and forth plane, he or she will probably make adjustments in the up and down plane. These adjustments cause small changes in reflected light, which result in slight changes in tone, but not enough to cause a problem with the reliability of the feedback provided to the operator by the present invention.

Figure 7:
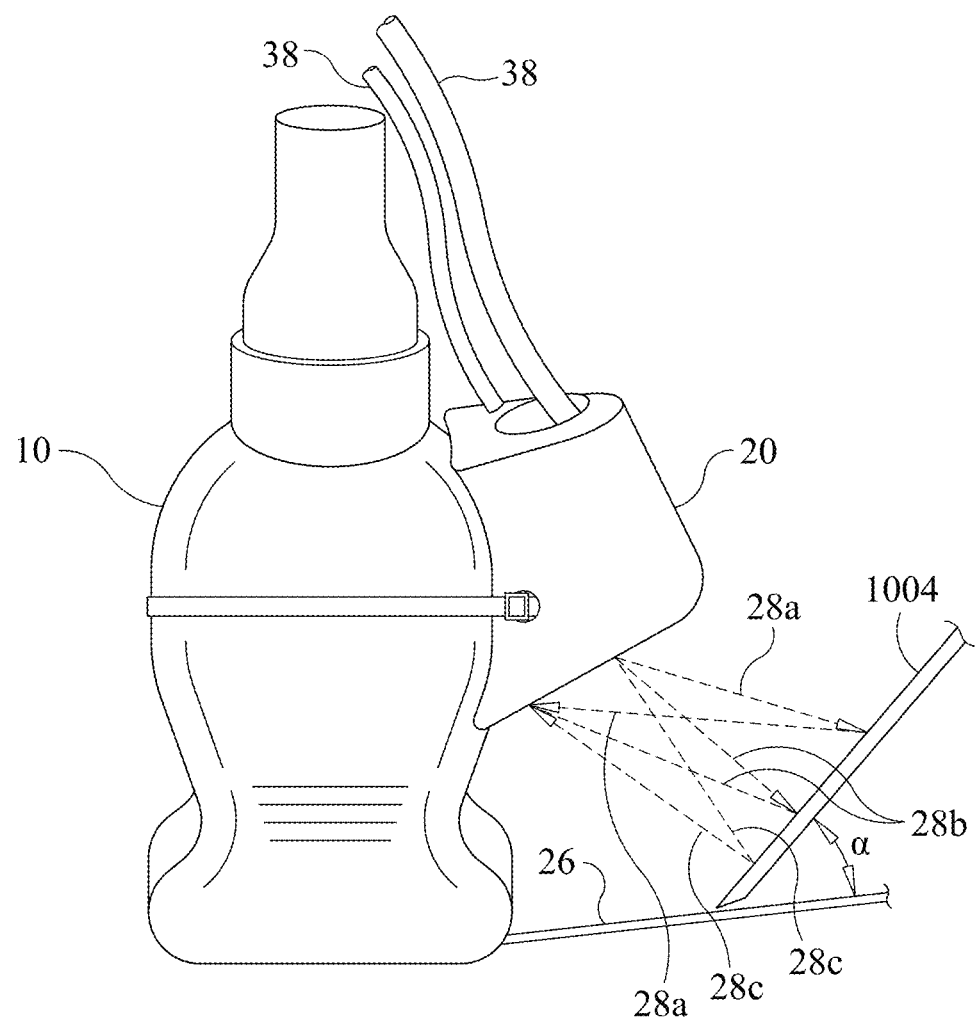
FIG. 7 illustrates insertion of a needle under the guidance of apparatus shown in FIG. 3, according to an embodiment of the present invention.

At event 608 the needle 1004 or other instrument is inserted into the skin 2 of the patient 1 at a location on the guide line 26, as illustrated in FIG. 7. The guide line 26 visually shows the operator of the needle 1004 where on the skin 2 to insert the needle 1004 or other instrument, i.e., at any location along the guide line 26. This provides a great deal more flexibility to the operator for choosing where to insert the needle/instrument 1004 compared to those apparatus that use a needle guide, since the needle guide allows only one location (or an extremely limited range of positions, along the plane on the skin) into which the needle can be inserted. The guide line 26 ensures that the needle 1004 or other instrument in inserted into the skin 2 at a location that is coplanar with the ultrasound plane. Light rays 28 (for simplicity, only light rays 28$a$, 28$b$ and 28$c$ are shown in FIG. 7) that are emitted by the emitter 22 contact the surface of the needle 1004 or other instrument at locations of the needle 1004 or other instrument that are in the plane of light emitted by the emitter 22 and are reflected by the needle 1004 or other instrument (wherein such other instrument has a light reflective surface) and some of these reflected light rays are directed toward and received by light receiver 24. The maximum amount of light received by the light receiver 24 occurs when the needle 1004 or other instrument is accurately aligned in the light plane which is the same plane as the plane of the ultrasound. The amount of light received by the light receiver 24 diminishes proportionally to the amount of misalignment of the needle 1004 or other instrument from the light plane.

Figure 2:
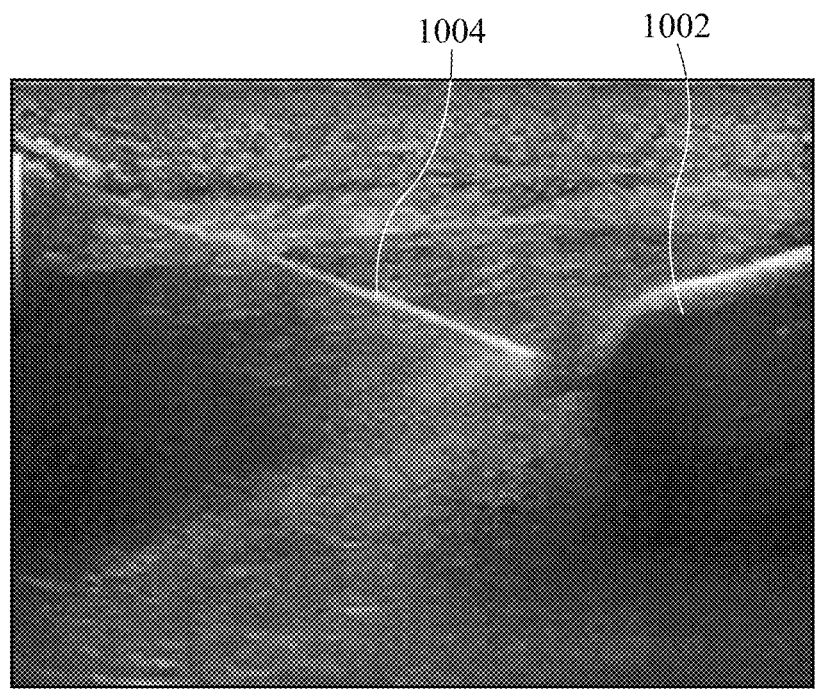
FIG. 2 is an ultrasound image showing a needle within the plane of the ultrasound beam.

As these relative values have already been calculated by processor 40 during calibration of the apparatus 100, when the needle 1004 or other reflective instrument is correctly aligned with the plane of the light beam, the amount of light received by light receiver is converted to a value that is sent as an electrical signal representative of that value to the processor 40. Having been calibrated, the processor 40 controls output of the control component to output one or more operator feedback outputs (visual and/or audio) so that the operator can be assured that the needle/instrument is currently in the proper orientation, coplanar with the light plane and ultrasound plane. This frees the operator from having to look at the needle/instrument 1004 to directly visually assess whether the needle/instrument 1004 is shining brightly as an indication that the needle/instrument 1004 is properly oriented. In this way, the operator can focus on viewing the ultrasound display 54 to concentrate on the image produced by the ultrasound system and does not have to be distracted by turning his/her attention to the instrument/needle 1004, which would requires breaking his/her direct visualization of and concentration on display 54, directly viewing the instrument/needle 1004 and adjusting it, if necessary, while viewing it, then attempting to hold the proper orientation of the needle/instrument 1004 while taking his/her eyes off of it and returning to directly viewing the ultrasound display 54. Rather, the operator can perform any adjustment function needed while maintaining a direct view of the ultrasound display and receiving audio feedback to confirm when the instrument/needle has been properly positioned. Since the control component 30 can also be positioned within the field of view of the operator while the operator views the ultrasound display 54, as shown in FIG. 5, for example, the operator can also view visual feedback from the control component via indicators 33 without turning away from his/her view of the ultrasound display. Additionally, the operator can view the instrument/needle 1004 on the ultrasound display as it enters the viewing field of the ultrasound probe 10, since the apparatus 100 makes it possible for the operator to maintain the instrument/needle 1004 in the plane of the ultrasound beam in a manner described above. Accordingly, upon entering the viewing field of the ultrasound beam(plane) the instrument/needle 1004 will appear visually on the display 54 in a manner similar to that shown in FIG. 2.

Figure 8:
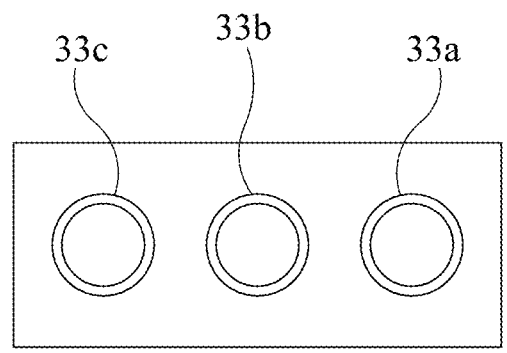
FIG. 8 illustrates visual indicators that can be used in an apparatus according to an embodiment of the present invention.

Once the apparatus has been calibrated and the needle/instrument is inserted into the skin 2 at event 608, some of the light reflected off of the instrument/needle 1004 is received by the light receiver 24 as noted above. The light receiver converts the light received to an electrical signal representative of the amount of light received, and send the electrical signal to the processor 40 at event 610. At event 612 the processor 40 controls the control component 30 to output one or more appropriate feedback signals that are interpretable by the operator. For example, if the instrument/needle is aligned with the light plane to an acceptable degree as determined by the calibration of the apparatus 100, the processor 40 controls the control component to light an indicator 33 that indicates that the instrument/needle 1004 is properly aligned. In the example shown in FIG. 8, the indicators 33 include a green indicator 33a, yellow indicator 33b and red indicator 33c which may be light emitting diodes or other light emitting devices. In this non-limiting example, the green indicator is lit when the amount of light received by the light receiver is an amount that equates to acceptable alignment of the instrument/needle 1004 with the light plane, whereas the yellow indicator 33b is lit when the instrument/needle 1004 is partially aligned, but not to an acceptable degree; and the red indicator 33c is lit when the needle/instrument 1004 is even further out of alignment from the plane than what exists at the time of actuating the yellow indicator 33b. Preferably only one indicator at a time is actuated. Additionally or alternatively, the speaker 32 can be actuated by the processor 40 in any of the manners described above, to audibly indicate to the operator whether the instrument/needle is positioned to an acceptable orientation relative to the light plane/ultrasound plane.

If the instrument/needle is not sufficiently aligned, the operator is alerted to this fact by the feedback outputted via the apparatus 100, and determines at event 614 that the instrument/needle 1004 is not sufficiently properly aligned. Then at event 616, the operator repositions the instrument/needle 1004 without the need to directly look at the needle/instrument 1004, and the processing returns to execute events 610 and 612. This processing loop 614-616-610-612 can be continuously repeated while the operator adjusts the orientation of the needle/instrument 1004, all the while receiving feedback from the control component, until such time as the operator receives feedback from the control component 30 that the instrument/needle has been properly positioned. When this determination is made at event 614, the operator then determines whether the instrument/needle 1004 has reached the target yet at event 618. This determination can be made primarily upon viewing the ultrasound display, since the target is visible in the ultrasound display, and the instrument/needle 1004, having been correctly placed in the plane of the ultrasound beam, is also visible in the ultrasound display.

When it is determined at event 618 that the target has been reached (such as by the operator viewing on the display 54 the piercing of the target by the needle 1004, for example) the insertion procedure ends at event 620. If the target has not yet been reached at this time of operation of event 618, then the operator advances the needle/instrument 1004 further into the patient toward the target. During this advancement, events 610 and 612 are carried out, with adjustment events 616-610-612-614 being carried out if needed.

By providing the visual and/or audible feedback from the control component 3o to the operator, this informs the operator in real time whether the needle/instrument 1004 is in the correct plane, allowing him or her to focus full visual attention on the ultrasound image 254 instead of dividing attention between the needle/instrument 1004 and the image 254.

Alternative to the arrangement shown in FIG. 5, the indicators 33 can be incorporated into the ultrasound display 54, so that the operator can view the visual indicators directly on the ultrasound display. Further alternatively, the processor 40 could be incorporated into the ultrasound processor 50, the audible feedback features 32 could be incorporated into the ultrasound apparatus and/or the guide and sensing component 20 could be incorporated into the probe 10.

Figure 9:
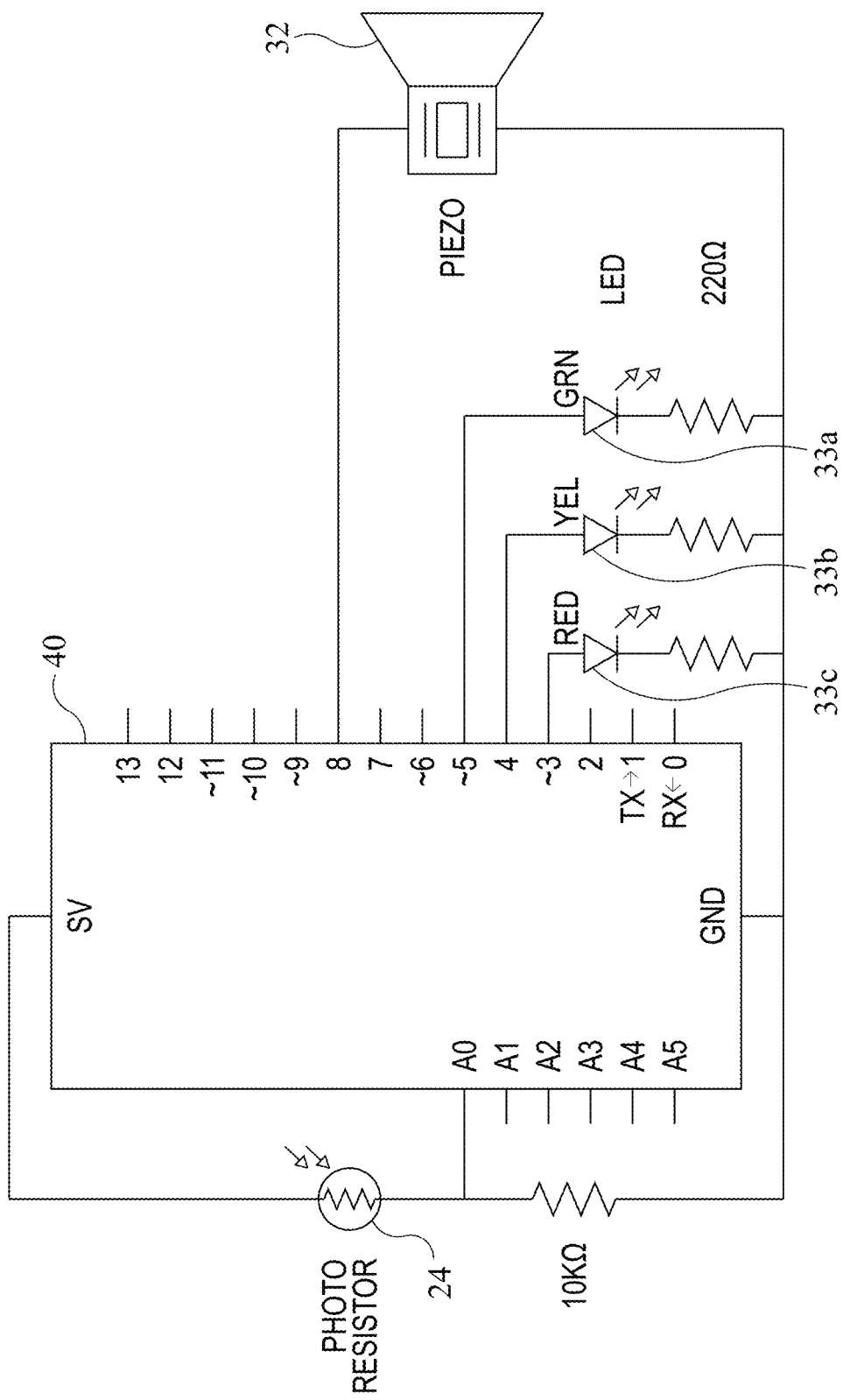
FIG. 9 shows a schematic of one preferred embodiment of elements of a control component as they relate to a light receiver, according to an embodiment of the present invention.

FIG. 9 shows a schematic of one preferred embodiment of elements of a control component 30 as they relate to light receiver 24 according to an embodiment of the present invention. In this embodiment, the processor 40 used was an Arduino Uno Rev 3, available at Arduino.cc-Main-Arduino-StarterKit.

Power connected to the photoresistor 24 actuates the photoresistor 24. The photoresistor 24 is connected to an analog pin (in this case, pin A0) on the processor 40. The resistance of the photoresistor decreases with increasing incident light, thereby allowing more current to reach A0. The analog pin senses and measures this input. Speaker 32 and visual indicators 33 are connected as outputs of the processor 40. In one specific example, pin 8 is connected to a piezo speaker 32 and pins 5, 4, and 3 are connected to green 33a, yellow 33b, and red 33c LEDs (light emitting diodes), respectively. Piezoelectric speakers and LEDs are readily available and in this instance, were include in the Arduino starter kit that included the Arduino Uno processor. The code that measures the photoresistor and instructs the piezoelectric speaker is a modification of code already in the public domain. It is called p06_LightTheremin and can be found as part of the free Arduino program under file→examples→10.starter kit→p06_LightTheremin.

In this example, the code programmed into the processor 40 instructs the piezo speaker 32 to play a high tone when reflected light is at a maximum, and a low tone when reflected light is at minimum, wherein the maximum and minimum values are determined by the values received from the photoresistor during calibration according to a calibration procedure described above. Likewise, the controller 40 instructs the green LED 33a to light when there is a large amount of reflected light, yellow 33b when there is medium reflected light, and red 33c when there is a small amount of reflected light, wherein the thresholds between large and medium and between medium and small are determined by the inputs received from the photoresistor 24 during calibration.

In this embodiment, to map out the range of high to low reflected light and subdivide it into high, medium and low ranges, the code contains a 5 second calibration phase prior to starting normal use. The needle is placed at the skin in the plane of the laser beam (for maximum reflected light), then calibration is turned on. During calibration, the user moves the needle back and forth, in and out of the beam. This establishes the range of light intensity it will see during normal use, and the device then switches to normal use mode. During normal use, there will be a high tone and the green LED will be illuminated when the needle is in the plane of the laser beam. If the alignment changes and the needle is no longer in the correct plane, the tone will decrease and the LEDs progress to yellow, then red depending on the degree to which it is out of alignment.

Figure 10:
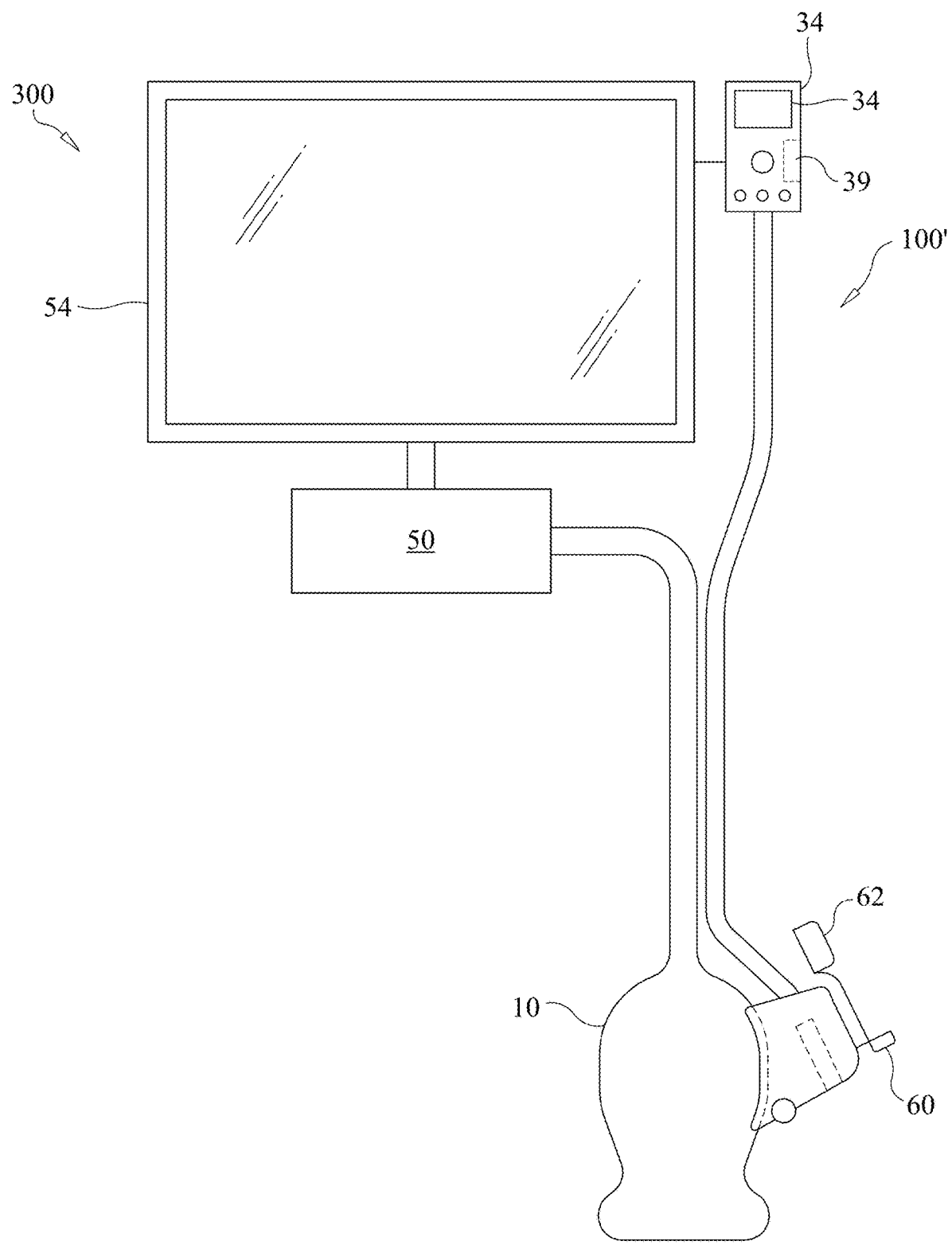
FIG. 10 is a schematic illustration of a system employing apparatus for guiding insertion of a needle or other instrument, according to an embodiment of the present invention.

FIG. 10 is a schematic illustration of a system 300 employing apparatus 100' for guiding insertion of a needle or other instrument, according to another embodiment of the present invention. It is noted that all components shown that are the same as those in the embodiment of FIG. 5 are not described here, as already having been described previously. System 300 may include all of the functionality of system 200, but additionally includes a camera 60 which can be mounted to or integral with the guide and sensing component 20. Camera 60 is oriented to view the guide line 26 on the skin 2 of the patient 1 when in use, and therefor also provides a view of the needle/instrument 1004 during use. The view is displayed on display 34 which is included in the control component 30 of this embodiment. Alternatively, display 34 could be incorporated into the display 54, so that the view from camera 60 could be displayed side by side with (or embedded in) the view provided by the ultrasound imaging. In the embodiment shown camera 60 communicates with a wireless receiver 39 (Wi-Fi, rf, BLUETOOTH® or the like) in control component 30 via a wireless sender 62 (Wi-Fi, rf, BLUETOOTH® or the like, corresponding to that used by the receiver 39). Alternatively, the camera 60 could be hard wired to the control component 30/controller 40.

Figure 11A:
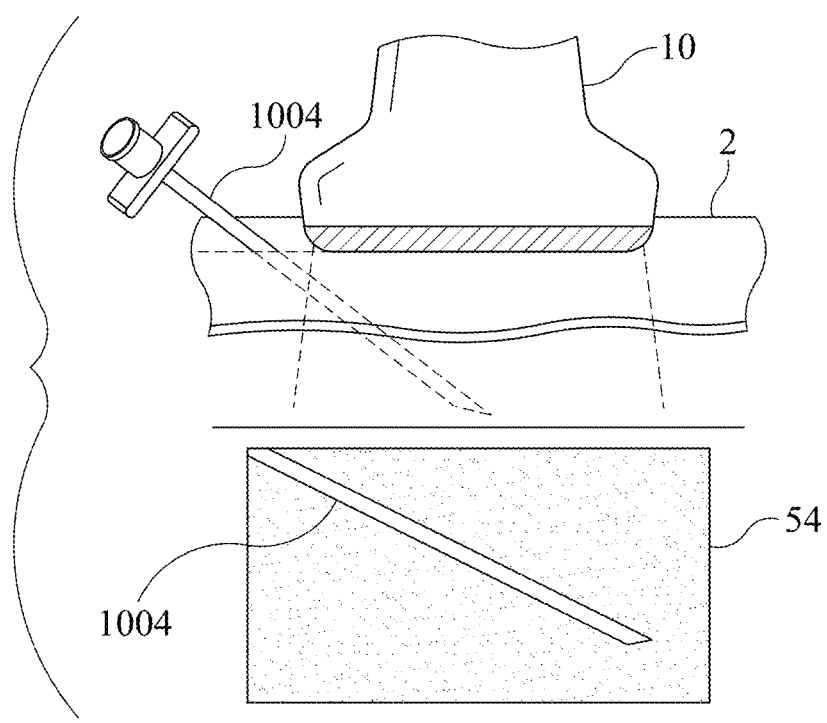
FIGS. 11A-11B illustrate differences between in plane and perpendicular/normal approaches for needle insertion.
Figure 11B:
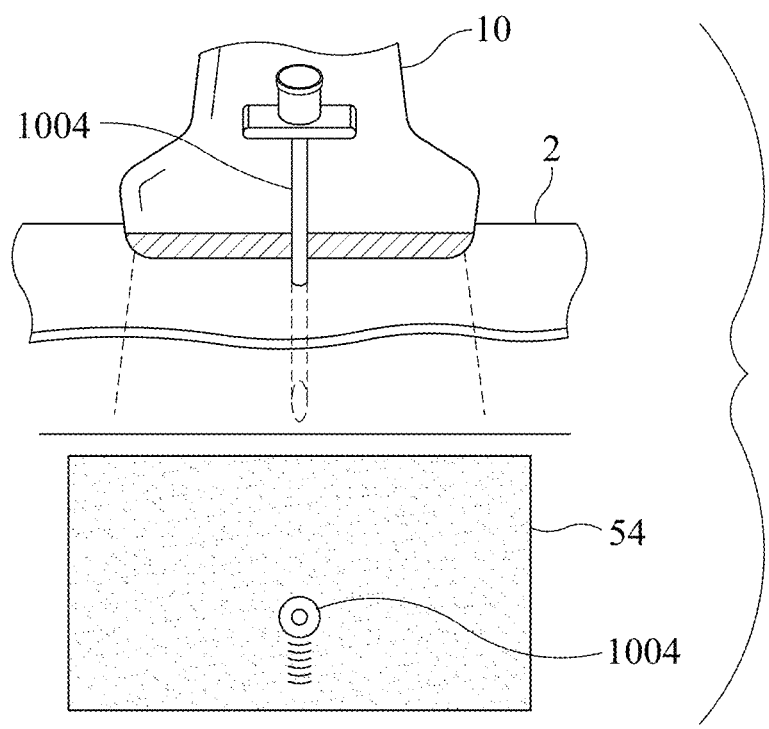

To this point, the embodiments described have been configured for the purposed of guiding a needle/instrument 1004 in the same plane as the ultrasound beam. However, it is noted that all of the embodiments described above can be modified so as to guide a needle/instrument 1004 in a plane that is at an angle to the plane of the ultrasound beam. The most common applications of such an arrangement are cases in which the needle/instrument is to be inserted along a plane that is normal or perpendicular to the ultrasound plane. For example, there are situations where it is safer and more effective for the needle/instrument 1004 to be in a plane that is perpendicular to the ultrasound beam. The perpendicular approach is sometimes called the out of plane approach. The difference between in plane and perpendicular/normal approaches is illustrated in FIGS. 11A and 11B. However, it is noted here that the present invention is not limited to in-plane and perpendicular approaches, as the light plane can be oriented at any angle between in-plane and perpendicular, for approaches where the angle is other than in-plane or perpendicular.

FIG. 11A illustrates the in plane approach, which has already been described in detail above. During this approach, the probe 10 is placed on the skin 2 of the patient and the needle/instrument 1004 is inserted into the skin 2 along a pathway and at an orientation in which the needle/instrument is substantially coplanar with the ultrasound imaging plane. The display 54 thus shows the entire length of the needle/instrument 1004 that has entered the ultrasound imaging field, which is coplanar therewith.

FIG. 11B illustrates the perpendicular or normal approach. During this approach, the probe 10 is placed on the skin 2 of the patient and the needle/instrument 1004 is inserted into the skin 2 along a pathway and at an orientation in which the needle/instrument 1004 is in a plane that is substantially perpendicular (normal) to the ultrasound imaging plane. Because during this approach the needle/instrument 1004 cuts across the plane of ultrasound imaging, the needle/instrument 1004 is only displayed in cross-section at the location where it intersects the ultrasound imaging plane. The display 54 thus shows only the substantially circular cross-section of the needle/instrument in FIG. 11B.

The perpendicular method can be particularly helpful for puncturing straight tubular structures like veins or arteries. Veins and arteries often run right next to one another, and the perpendicular method helps make sure that the correct one is punctured. Though somewhat less intuitive for the operator, this helps avoid the potentially disastrous complication of, say, placing a large dialysis catheter in the carotid artery instead of the jugular vein. The apparatus 100 can be very helpful in guiding needles/instruments in the perpendicular approach as well.

Figure 12:
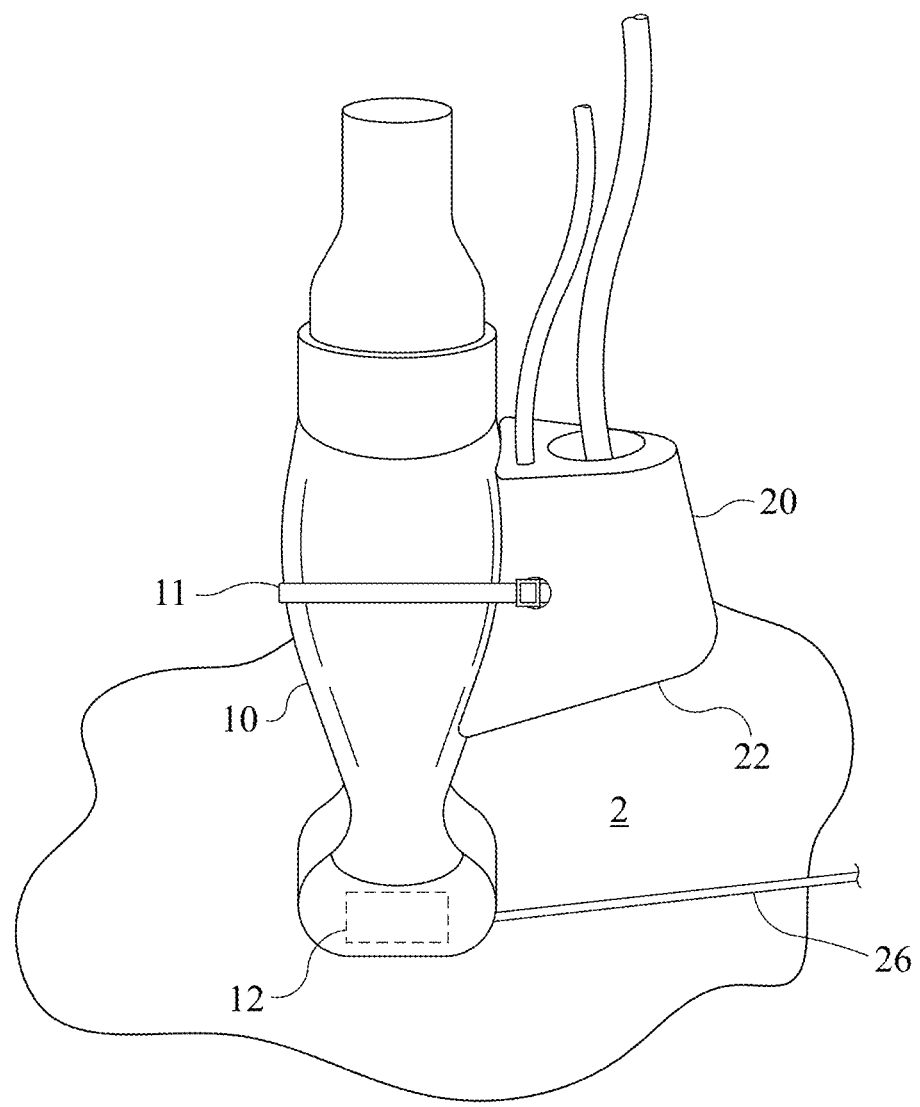
FIG. 12 shows, a guide and sensing component of an apparatus for guiding insertion of a needle or other instrument, according to an embodiment of the present invention.

FIG. 12 shows, a guide and sensing component 20 of an apparatus 100 for guiding insertion of a needle or other instrument, according to an embodiment of the present invention. This embodiment is similar to that shown in FIG. 3 except that the guide and sensing component is mounted to ultrasound probe 10 in a position oriented so that the guide line 26 is displayed on the skin 2 of the patient such that it is perpendicular to the plane of the ultrasound beam, as the component 20 is mounted so that the beam of the emitter 22 is perpendicular (normal) to the ultrasound beam emitted by the transducer 12 of the probe 10. The component 22 can be positioned such that the guide line 26/light plane of the emitter 22 intersects with the point on the probe 10 that is in the middle of the ultrasound image/ultrasound viewing plane. The probe 10 can be positioned so that the target (e.g., blood vessel) appears as a circular structure in the midpoint of the image on the display 54. Then the needle/instrument 1004 is inserted into the skin 2 next to the probe and on the guide line 26 and is kept in the light plane of the light emitter in the same manners that this can be performed as described above with regard to in plane embodiments. Thus the instrument/needle can be advanced diagonally downward to puncture the target/vessel where it crosses the ultrasound beam. Again, the operator keeps the light shining along the length of the needle/instrument 1004, confirmed by audio and or visual feedback. Used this way, the apparatus 100 helps guide the needle/instrument 1004 into the target/vessel in a single controlled pass, avoiding puncturing the skin 2 to one side or the other of the target/vessel, and keeping it in the line of the target/vessel.

Figure 13:
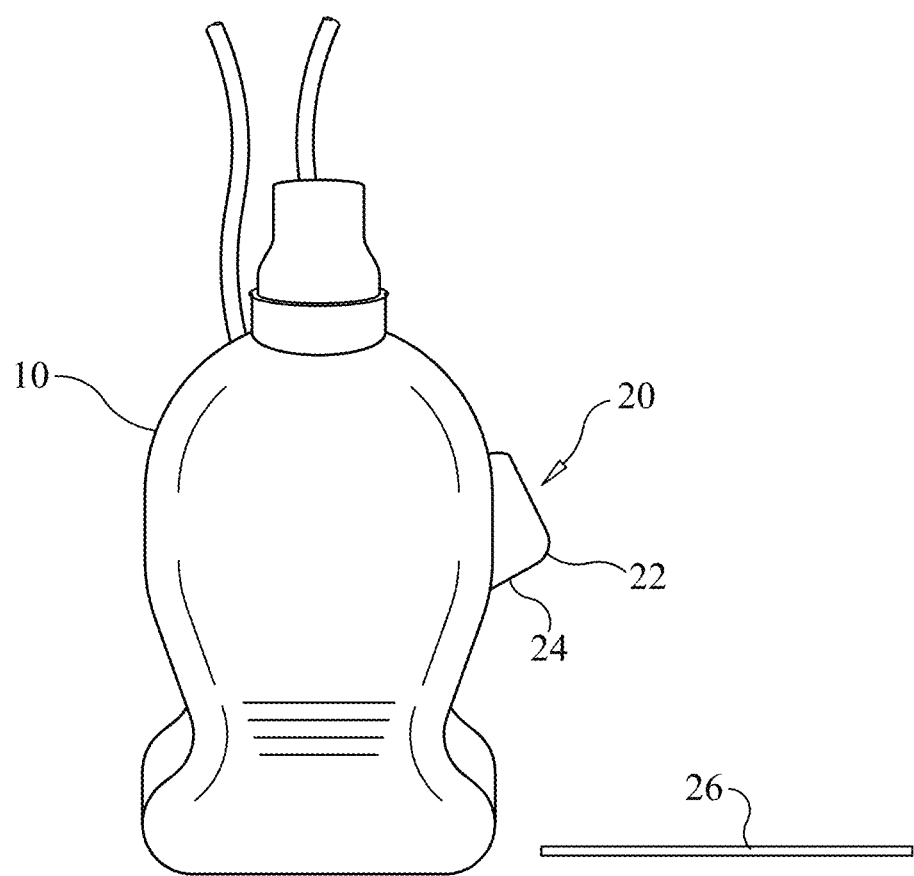
FIG. 13 shows a probe in which the guide and sensing component are integrated into the structure of the probe, according to an embodiment of the present invention.

Various embodiments of apparatus 100, 100' can be provided. To make the apparatus 100, 100' usable with most, if not all existing ultrasound probes, attachable versions can be provided, which can be attached by attachment means 11, that include any such means as described above, or their equivalents. The housing of the guide and sensing component 20 can be shaped to interface with the shape of a probe 10 to which it is to be attached, such as by 3D printing, molding, machining or the like. Alternatively, the guide and sensing component could be integrated into the structure of a probe 10. An example of an embodiment of a probe 10 in which the guide and sensing component are integrated into the structure of the probe is shown in FIG. 13, which shows the light source 22 and light receiver 24 integrated into the structure of the probe 10. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An assembly for guiding a needle or other instrument comprising:
    an imaging component comprising a transducer that projects a planar imaging beam into an imaging plane;
    an instrument monitor comprising a source of illumination that projects a light beam into a light plane and a light receiver aligned with said light plane and configured to quantify an amount of light reflected from an object in said light beam to said light receiver;
    a processor configured to determine whether the object is aligned in said light plane, based upon a quantity of light received by said light receiver, wherein the processor determines the object to be aligned in said light plane based on the quantity of light received by said light receiver being greater than or equal to a predetermined quantity of light; and
    output means configured to output information to notify a user whether the object is aligned in said light plane, wherein said output means is configured to be used to notify the user without a need for the user to look at the object to be notified, regardless of a location of said output means.

2. The assembly of claim 1, wherein said transducer comprises an ultrasound transducer that projects a planar ultrasound beam into an ultrasonic imaging plane.

3. The assembly of claim 1, wherein said light receiver comprises a photoresistor.

4. The assembly of claim 1, wherein said output means comprises a visual indicator, wherein a first visual indication is displayed when the object is aligned in said light plane and a second visual indication, different from said first visual indication, is displayed when the object is not aligned in said light plane.

5. The assembly of claim 1, wherein said output means comprises an audio indicator, wherein a first audio signal is outputted when the object is aligned in said light plane and a second audio signal, different from said first audio signal, is outputted when the object is not aligned in said light plane.

6. The assembly of claim 1, wherein said instrument monitor further comprises:
    a camera oriented to view the object and a guide line projected onto the skin of a patient by said light beam; and
    a display configured to display images taken by said camera.

7. The assembly of claim 6, further comprising a display configured to display images generated by said imaging component, wherein said display configured to display images taken by said camera is positioned adjacent to, or integrated with said display configured to display images generated by said imaging component.

8. The assembly of claim 1, wherein said instrument monitor is oriented relative to said imaging component such that said imaging plane is coplanar with said light plane.

9. The assembly of claim 1, wherein said instrument monitor is oriented relative to said imaging component such that said imaging plane is out of plane relative to said light plane.

10. An instrument monitoring apparatus, said apparatus comprising:
    a guide and sensing component configured to be attached to an ultrasound probe; said guide and sensing component comprising:
        a source of illumination configured to project a planar light beam; and
        a light receiver aligned with the planar light beam and configured to quantify an amount of light reflected from an object in the planar light beam to the light receiver by receiving said amount of light and converting said amount of light to an electrical signal; and
    a control component comprising:
        a processor configured to receive said electrical signal from said light receiver, and based on a magnitude of said amount of light represented by said electrical signal being greater than or equal to a predetermined magnitude, determine whether the object is sufficiently within said planar light beam; and
        output means, wherein said processor instructs said output means to output a first signal when it is determined that the object is sufficiently within said planar light beam, and wherein said processor instructs said output means to output a second signal that is distinct from said first signal, when it is determined that the object is not sufficiently within said planar light beam.

11. The apparatus of claim 10, wherein said light receiver comprises a photoresistor.

12. The apparatus of claim 10, wherein said guide and sensing component further comprises a camera oriented to view the object and a guide line projected onto the skin of a patient by said light beam; and
    wherein said control component further comprises a display configured to display images taken by said camera.

13. The apparatus of claim 10, wherein said output means comprises a speaker.

14. The apparatus of claim 10, wherein said output means comprises lights.

15. The apparatus of claim 14, wherein said lights comprise a first light configured to illuminate in a first color, and a second light configured to illuminate in a second color different from said first color.

16. A method of guiding an instrument to a target location inside a body of a patient, said method comprising:
    contacting an ultrasound probe to skin of the patient and positioning the ultrasound probe so that the target is shown in a display of an ultrasound system that includes the ultrasound probe;

displaying a visible guide line on the surface of the patient's skin by emitting a light beam from an instrument monitoring apparatus mounted on or integral with the ultrasound probe;

contacting the instrument to the skin of the patient at a location along the guide line;

orienting the instrument, with guidance by feedback, so that the instrument is sufficiently in a plane of the light beam, as confirmed by at least one of an audible or visual feedback signal outputted by the instrument monitoring apparatus in a manner such that an operator of the ultrasound system does not have to interrupt viewing of the display of the ultrasound system in order to interpret the at least one audible or visual feedback signal, wherein light rays reflected off the instrument in the guide line is received by a light receiver aligned with the guide line and wherein the instrument is determined to be properly oriented based on a quantity of light received by said light receiver being greater than or equal to a predetermined quantity of light;

inserting the instrument through the skin and toward the target;

wherein the light rays emitted by the instrument monitoring apparatus that impact the instrument and are reflected back to the light receiver of the instrument monitoring apparatus are converted to electrical signals representative of amounts of light reflected from the instrument, and the electrical signals are continually monitored by a processor of the instrument monitoring apparatus during said inserting;

wherein the processor instructs a first audible and/or visual feedback signal to be outputted when it is determined that the quantity of light reflected is representative of the instrument being sufficiently in the light plane;

wherein the processor instructs a second audible and/or visual feedback signal that is distinguishable by the user from the first audible and/or visual feedback signal, to be outputted when it is determined that the quantity of light reflected is representative of the instrument being insufficiently in the light plane;

said method further comprising temporarily halting said inserting and adjusting the orientation of the instrument any time that said second signal is outputted, said adjusting continuing until such time as said first signal is again outputted; and continuing said inserting and adjusting as needed, until the target is contacted or pierced by the instrument, as verified by ultrasonic imaging viewed on the display of the ultrasound system.

17. The method of claim 16, wherein a plane of an ultrasound beam emitted by the ultrasound probe is coplanar with a plane of the light beam.

18. The method of claim 16, wherein a plane of an ultrasound beam emitted by the ultrasound probe is normal to a plane of the light beam.

19. The method of claim 16, wherein the instrument monitoring apparatus further includes a camera and a camera display configured to display images taken by the camera, said method further comprising viewing the instrument and the guide line by the camera pm the camera display, wherein the camera display is positioned in a location for viewing by the operator without having to discontinue viewing the display of the ultrasound system.

20. The method of claim 16, further comprising calibrating the instrument monitoring apparatus, prior to said inserting, wherein said calibrating comprises:

after said contacting the instrument to the skin, aligning the instrument in the plane of the light beam by directly visually confirming an orientation where the instrument appears brightest, due to a maximum amount of light reflected from the instrument; and angling the instrument in and out of the light beam by varying degrees;

wherein an amount of light received by the light receiver when the instrument is in the plane is converted to a signal representative of a maximum amount of light that will be received by the light receiver, and light amounts reflected by the various positions wherein the instrument is angled to various degrees out of the line plane are converted to signals representative of the varying lesser amounts of light that are received by the light receiver resulting from the varying positions;

wherein the signals converted by the light receiver are sent to the processor, and the processor establishes a range of signals corresponding to a range of light intensity values that will be received by the light receiver during normal use; and wherein the processor subdivides the range of signals to a subset of the range that indicates that the instrument is sufficiently within the light plane, and at least one subset of the range that indicates that the instrument is not sufficiently within the light plane.

21. The method of claim 16, wherein the instrument comprises a needle.

* * * * *